United States Patent
Li et al.

(10) Patent No.: US 6,878,553 B1
(45) Date of Patent: Apr. 12, 2005

(54) DEVICE AND METHOD FOR CONCENTRATION OF SAMPLES BY MICROCRYSTALLIZATION

(75) Inventors: Sam Fong Yau Li, Singapore (SG); Hong-ping Wei, Singapore (SG)

(73) Assignee: The National University of Singapore (SG)

( * ) Notice: Subject to any disclaimer, the term of this patent is extended or adjusted under 35 U.S.C. 154(b) by 0 days.

(21) Appl. No.: 09/831,551
(22) PCT Filed: Nov. 10, 1999
(86) PCT No.: PCT/SG99/00117
§ 371 (c)(1), (2), (4) Date: Aug. 6, 2001
(87) PCT Pub. No.: WO00/29102
PCT Pub. Date: May 25, 2000

(30) Foreign Application Priority Data
Nov. 12, 1998 (SG) .............................. 9804033

(51) Int. Cl.⁷ .......................... G01N 1/00; B01D 11/04
(52) U.S. Cl. ...................... 436/174; 436/180; 436/181; 422/245.1; 422/260; 422/943
(58) Field of Search ................................ 436/174, 180, 436/181; 422/245.1, 260, 943

(56) References Cited

U.S. PATENT DOCUMENTS

| | | | | |
|---|---|---|---|---|
| 3,918,916 A | * | 11/1975 | Garrett ..................... | 422/245.1 |
| 4,055,457 A | * | 10/1977 | Swinehart .................... | 117/76 |
| 4,335,581 A | | 6/1982 | Nail | |
| 4,747,700 A | * | 5/1988 | Lenz et al. .................. | 374/135 |
| 4,772,487 A | * | 9/1988 | Gotoh et al. ............... | 427/2.13 |
| 5,056,427 A | * | 10/1991 | Sakabe et al. .............. | 100/211 |
| 5,459,300 A | * | 10/1995 | Kasman ....................... | 219/433 |
| 5,475,610 A | * | 12/1995 | Atwood et al. ............. | 700/269 |
| 5,702,672 A | | 12/1997 | DeWitt | |
| 5,888,830 A | * | 3/1999 | Mohan et al. ............... | 436/174 |
| 6,342,185 B1 | * | 1/2002 | Dahl et al. ................ | 422/82.12 |
| 6,485,692 B1 | * | 11/2002 | Freitag et al. .............. | 422/130 |

FOREIGN PATENT DOCUMENTS

| | | | | |
|---|---|---|---|---|
| DE | 19739120 A1 | * | 3/1999 | ........... G01N/31/22 |
| GB | A2336908 | | 11/1999 | |
| GB | 2336908 | | 11/1999 | |
| WO | A1-9851393 | | 11/1998 | |
| WO | WO/9851393 A1 | | 11/2001 | |

OTHER PUBLICATIONS

"Determination of Trace Amount of Organic Solvent in Water By Freezing Precencentration Gas Chromatography" By Zhou Zhihang, Zheng Enhua, Feng, Daren; Nanjing Huagong Xueyuang Xuebao, vol. 16, No. 1 (Jan. 1994) pp. 67–71 abstract only.

"Determination of Anion Impurities in High–Pure Water Using Ionic Chromatography with Preliminary Chrystallization Concentration" By V.V. Aliseichik, A.B. Blank and L.V. Vasetskaya; Khim. Tekhnol. Vody. vol. 14, No. 9 (Sep. 1992), pp. 674–712 abstract only.

* cited by examiner

*Primary Examiner*—Yelena G. Gakh
(74) *Attorney, Agent, or Firm*—Birch, Stewart, Kolasch & Birch, LLP (57) ABSTRACT

A device and method for simultaneously concentrating a plurality of samples in small volumes based on the principle of cystallization. The device comprises a device for concentrating a plurality of samples comprising: a first temperature control means (12) having a plurality of container means (40/50) for containing said plurality of samples; a second complementary temperature control means (11) having a plurality of conducting means (22) which are adapted to be inserted in respective samples in said plurality of container means (40/50); and insulating means (30) for insulating said first temperature control means (12) from said temperature control means (11) such than an amount of heat from said plurality of samples is dissipated through said plurality of conducting means (22).

12 Claims, 7 Drawing Sheets

DEVICE AND METHOD FOR CONCENTRATION OF SAMPLES BY MICROCRYSTALLIZATION

This application is the national phase under 35 U.S.C. § 371 of PCT International Application No. PCT/SG99/00117 which has an International filing date of Nov. 10, 1999, which designated the United States of America and was published in English.

BACKGROUND OF THE INVENTION

1. Field of the Invention

The present invention relates generally to the field of sample handling and to sample preconcentration. More particularly, this invention relates to a method and device for concentration of samples, such as analyte solutions, on the principle of crystallization.

2. Description of the Prior Art

In order to meet the requirement of current environmental, biochemical and clinical analysis, where more information is needed to be drawn from a small amount of samples, such as blood or a solution containing quite small amount of interesting compounds, suitable devices and methods need to be developed for handling and concentrating these samples. The most widely used methods currently are based on extraction, such as solid phase extraction, solid phase microextraction, and liquid—liquid extraction. There are also other methods which could be used, such as evaporation. There is hardly any method for concentrating sample solutions based on the principle of crystallization.

When a crystalline phase is formed from a fluid phase, the process is commonly called crystallization. Due to the high selectivity by which atoms, ions, and molecules may be built in a crystal lattice, crystallization has been used in industry for producing high purity compounds. With the selected compounds (usually the major component in the liquids, such as water in aqueous solutions and organic solvents in organic solutions) crystallizing out from the liquid and becoming purified, the other compounds (usually the minor components in the liquid, or analytes when they are the compounds of interest) become concentrated in the remaining liquid. Freeze concentration is a process for concentrating aqueous solutions by removing water in the form of ice. Using crystallization to concentrate samples can provide several advantages over other concentration techniques often used in analytical chemistry, such as extraction and evaporation. Compared with methods of extraction, no organic solvent or any other reagents are needed during crystallization, which will reduce the danger of contamination to samples and the cost for disposing toxic reagents. Compared with evaporation, crystallization can be used to concentrate semi-volatile and volatile samples. In addition, crystallization can concentrate analytes in solid samples which can be changed into liquid state under certain conditions, such as heating them to a certain temperature. Few concentration techniques in current analytical chemistry can concentrate solid samples directly. Until now, there are only a few papers available which address concentration and analysis of organic solvents and anions in aqueous solution based on freeze concentration. The process of freeze concentration is usually quite long, generally several hours, and generally requires large sample solutions (at least several mL).

Recently, with the intense pharmaceutical drug discovery efforts, combinatorial chemistry is offering great challenges to analytical chemistry. Combinatorial chemistry is a style of synthesis in which selected building blocks are combined in different ways so as to produce large numbers, or libraries, of new molecular variants much more efficiently than is possible by traditional synthetic approaches (Chem. Rev., March 1997). It has given drug discovery units in pharmaceutical companies a crank with a very long handle, producing in a few days a 50,000-compound library of new molecular structures. Subsequently compounds showing activity of the kind sought and their structures will need determining. In addition, most combinatorial methodologies yield only 0.1 to micromole quantities of product, which are localized on polymer beads, plastic "pins", or in microtiter plate wells. Thus, very high analytical sensitivities are demanded. The method described in the present invention which can concentrate analytes in small volumes and concentrate hundred or thousand of them simultaneously could be very useful and highly desirable.

SUMMARY OF THIS INVENTION

The present invention is directed to a method and device which can simultaneously concentrate a plurality of samples in small volumes based on the principle of crystallization.

In one embodiment, there is provided a device for concentrating a plurality of samples comprising:

a first temperature control means having a plurality of container means for containing said plurality of samples;

a second complimentary temperature control means having a plurality of conducting means which are adapted to be inserted in respective samples in said plurality of container means; and insulating means for insulating said first temperature control means from said second temperature control means such that an amount of heat from said plurality of samples is dissipated through said plurality of conducting means.

According to another embodiment there is provided a method for concentrating a plurality of samples comprising:

placing a plurality of samples in a first temperature control means having a plurality of container means for containing said plurality of samples;

inserting a conducting means into each of said samples, said conducting means eing mounted relative to a second complimentary temperature control means;

cooling said plurality of samples by means of said first and second temperature control means to selectively crystallize components of said samples; and removing said crystallized components from said samples.

The first and second temperature control means may include any suitable means for controlling the temperature of the plurality of samples. In a preferred embodiment, the first and second temperature control means comprise first and second cooling means. More preferably, each of the first cooling means and second cooling means comprises thermostat controlled cooling means for providing a constant temperature, a stable variable temperature, a temperature gradient, or a series of temperature gradients. In certain embodiments, the first and second temperature control means are individually selected from circulating heaters and coolers, heating and cooling blocks and slush baths.

In a preferred embodiment, the plurality of container means are located in a face of the first temperature control means, and the insulating means comprises a layer of insulating material disposed on a face of the second temperature control means opposing the face of the first temperature control means on which the plurality of container means are located. Most preferably, the plurality of conducting means passes from the second temperature control means through the insulating material and, in use, into the plurality of samples in the plurality of container means.

The insulating means preferably partly or completely prevents transfer of heat between the first temperature control means and the second temperature control means. In a particularly preferred embodiment, the insulating means comprises a plastic foam insulator.

The conducting means may comprise any suitable conducting material, and may be of any suitable form which facilitates the conduction of heat from the sample through the conducting means. Preferably, the plurality of conducting means comprises a plurality of wires. The wires may be formed from metal, polymer, inorganic or organic material, and preferably comprise copper wires, each wire optionally comprising an outer protective layer. Furthermore, each of the wires may include a single wire, or may include a plurality of wires. Preferably, each of said wires has a diameter of from about several nanometers to several centimeters. More preferably, each of the wires has a diameter of about 1 millimeter.

The container means may comprise any suitable means for containing the plurality of samples. In a preferred embodiment, the container means comprises a plurality of wells, each of which receives one of the plurality of samples or is adapted to receive a sample container holding one of the plurality of samples. In this regard, the samples may be introduced directly into the wells, or may be placed into sample containers which are in turn placed in the wells. In the latter case, it is preferred that each sample container comprises a tube, bottle or vial. In a particular embodiment, the sample container comprises a dialysis tube.

Once the samples are in place, the first and second temperature control means are generally moved from a loading position to an operative position in which the conducting means are inserted into respective samples. This may be achieved either manually or automatically as desired.

In use, the conducting means, having been inserted in respective samples, and advantageously act as a support for nucleation during the crystallization. Further, in a preferred embodiment, as the crystallized components are crystallized on the conducting means acting as a support, the conducting means advantageously facilitates removal of the crystallized components from the container means.

The crystallization of components of the samples will, as will be readily understood by a person skilled in the art, be carried out at a temperature which is dependent on the characteristics of the samples, and the desired final concentrate. However, the crystallization will generally be carried out at a temperature of from −70° C. to about 0° C.

As will be understood by a person skilled in the art, the samples may take any suitable form. In particular, the present invention may be used to concentrate various aqueous solutions, organic solutions, or solids which can be liquefied under certain conditions, for example at elevated temperature.

The solutions remaining in the sample containers are concentrated solutions which may be used for further analysis by other analytical instruments. Another cycle of concentration may also be carried out after the crystals on the wires are removed by heating or other methods.

While those skilled in art will recognize that there exists a multitude of applications a relevant to the present invention, the invention will now be described in the context of the analysis of aqueous samples by freeze concentration, a particularly suitable application of the present invention.

Additional features, aspects and advantages of certain embodiments of the invention will be more fully understood when considered in connection with the accompanying drawings and the detailed description which follows.

The term "thermostat" as used hereafter refers to a temperature regulated cooling device.

DETAILED DESCRIPTION OF A PREFERRED EMBODIMENT

Figure 1:
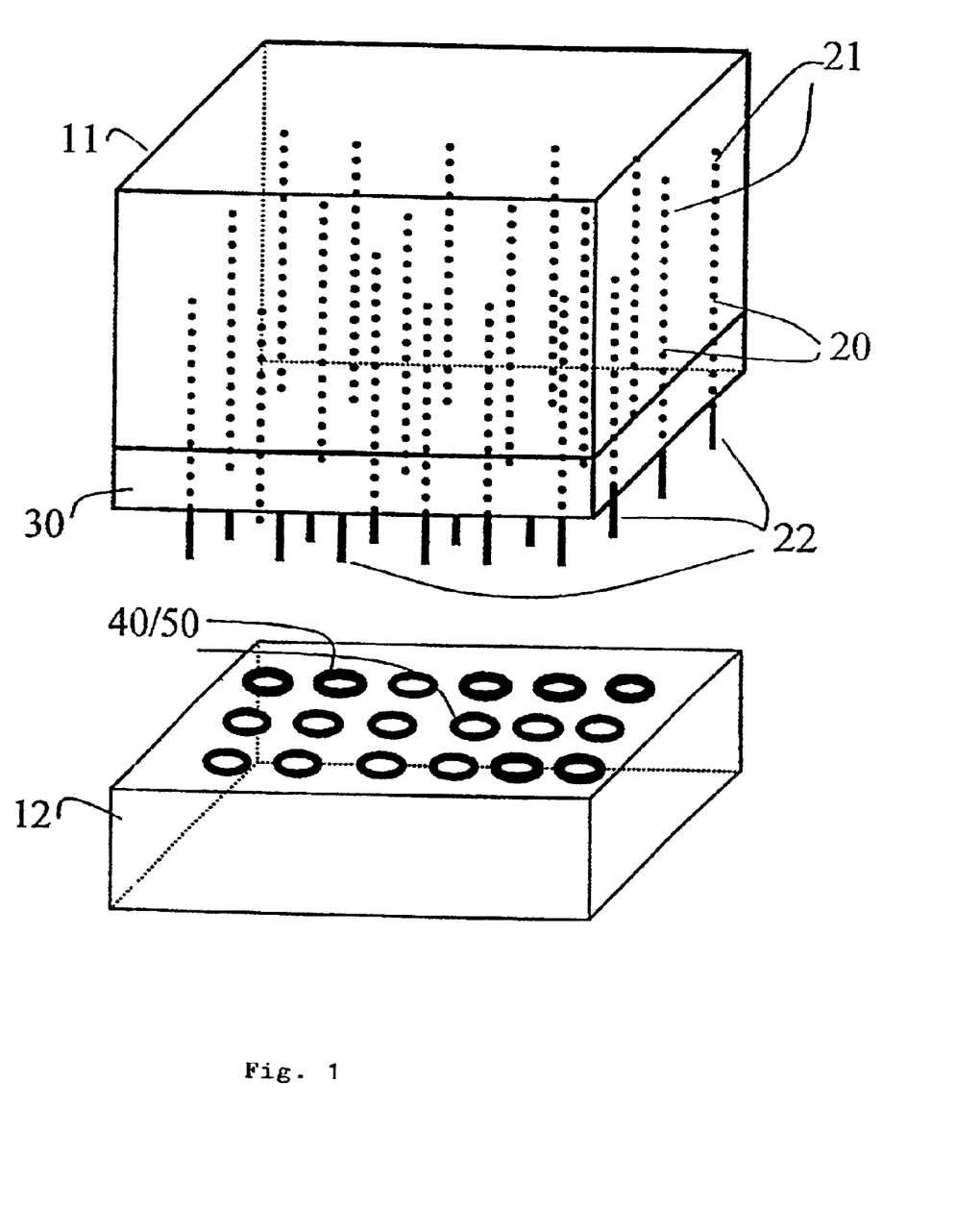
FIG. 1 is a schematic diagram of the device of the present invention for concentration of a plurality of sample solutions simultaneously by microcrystallization. Only 3×6 array is shown for demonstration. The real device can be as much as 100×100 or more.

Referring to FIG. 1, a device for carrying out microcrystallization has two A, thermostats 11 and 12 for controlling temperatures, a plurality of wires 20 for conducting heat, a thermal insulator 30 between the thermostats 11 and 12, and a plurality of sample containers 50. Each of the wires 20 has two ends 21 and 22. The wires 20 are immobilized vertically and individually on the bottom of the thermostat 11 in an array so that their ends 21 are located in the thermostat 11 and their ends 22 lie outside the thermostat 11. The wire ends 22 also pass through the thermal insulator 30 which is immobilized on the outside bottom of the thermostat 11. On the top of the thermostat 12, a plurality of wells 40 are created in the same array pattern as that for the wires 20. The size and shape of the wells 40 should match the size and shape of the sample containers 50 so that the sample containers 50 can be put in and taken out easily from the wells 40 and there are little spaces between them when the containers 50 are in the wells 40. If the wells 40 can be removed from the thermostat 12, the well 40 can be sample containers also. The sample containers 50 could have caps or no caps. In either way, the top of each of the sample containers 50 has a hole or space whose size is larger than any other inner space of the sample containers 50 so that the crystal produced can be removed with the wires 20 from the sample containers 50.

Figure 2:
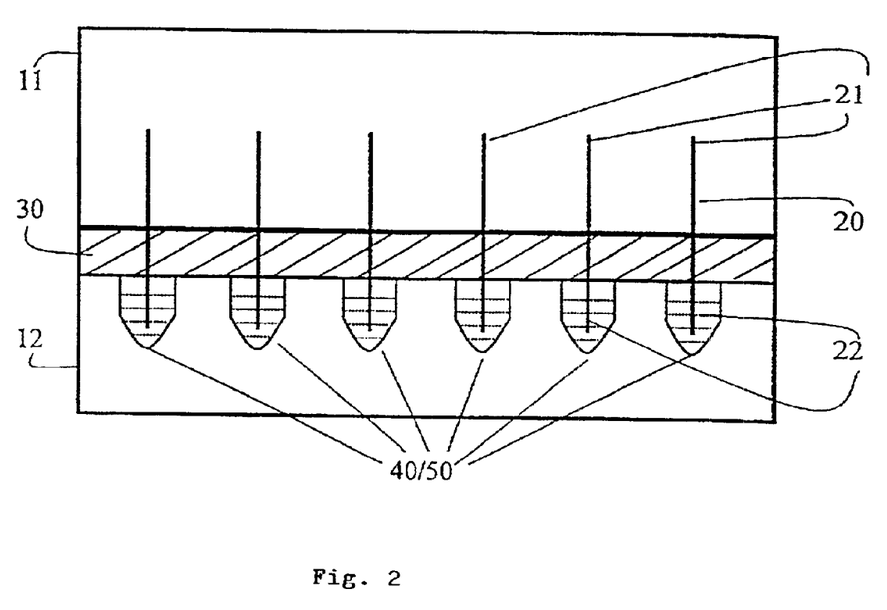
FIG. 2 is a schematic diagram of partial section view taken along one row of the sample containers when the device in FIG. 1 is in operation.

For operating the device of the present invention, sample solutions with known volumes or solid samples with known weights are filled into the sample containers 50 first. Then containers 50 with the samples are put into the wells 40 individually. Finally, the thermostat 11 moves down so that each of the wire ends 22 is inserted into the individual sample containers 50 and immersed into the sample solutions. FIG. 2 illustrates the relative positions of the thermostats 11 and 12, the sample containers 50 and the wires 20 at this stage. The temperature of the thermostat 12 is adjusted to set the temperature of the sample solutions in the sample containers 50, whereas the temperature of the thermostat 11 is adjusted to an appropriate temperature at which the major components in the sample solutions will crystallize out. Time is recorded in order to control the time for the concentration. Finally, when most of the sample solutions in the sample containers 50 attain crystalline state, the thermostat 11 moves up. The crystals produced will be removed, along with the wires 20, from the sample containers 50. The concentrated solutions will remain in the sample containers and can be moved with the sample containers 50 for further analysis. For another cycle of concentration, the crystals outside the wires 20 from the latest process can be removed by heating or other means. After washing the wire ends 22, the same procedure as described above can be used again.

As discussed above, the thermostats 11 and 12 can be any apparatuses that can control temperature. For example, circulating heater and cooler, heating or cooling blocks, thermoelectric devices, slush baths (low-melting-point liquids kept in a partially frozen state by either liquid nitrogen or dry ice), and many others apparatus known to those skilled in the art. The choice of the thermostats depend on the temperature needed for crystllization. Usually the temperature given by the thermostat 12 should be in the range of tempers between which the sample will be in liquid state, while the temperature given by the thermostat 11 should be in the range of temperatures between which the major components of the sample will be crystallized out. For example, when aqueous solutions need to be concentrated, the thermostat 11 can be those which can control its temperature below 0° C. because the freezing point of water is 0° C., and the thermostat 12 can be those which can control the temperature above 0° C. The heat produced in the sample containers 50 during formation of ice can be drawn through the wires 20 into the thermostat 11 and be dissipated. In such way, the ice can only form first on the outside of the wire ends 22 and then grow further into the other area of the solution. At the final stage, ice can be easily separated from the concentrated solutions because it will be removed together with the wires 20. If desired, the freeze concentration process may be accelerated by choosing a thermostat 11 which can generate a much lower temperature, for example, −70° C., or a thermostat 12 which can generate a temperature quite near 0° C. It will be seen in the following examples that the growth rate of ice may be controlled in this way.

For purpose of conducting heat and separating the crystal produced, the preferred wires 20 should be those having good thermal conductivity and good mechanic strength. Metal wires, especially copper wires, usually is a good choice. However, other materials, such as polymers, can be used also. The diameter of the wires 20 can range from centimeters to several micrometers, or even to nanometers, depending on the volume or the amount of the sample needed for concentration. For small volumes of samples, thin wires 20 are preferred. Other considerations could be whether the material used will cause contamination or other unwanted effects to the samples because of contact of the wire ends 22 with the samples. For example, copper wire could be a problem for use to concentrate copper ions in aqueous solutions. Sometimes copper ions can cause damage to the activities of some enzymes. In such cases, a thin layer of another material is coated to the copper wires, or copper wires are not used.

The choice of sample containers 50 also depends on the samples needing concentration. For samples with small volumes, small containers are preferred. For some solid samples such as phenols, the material of the sample containers should be able to withstand the temperature used to melt the solid samples. For the purpose of separating the crystal from the concentrated solutions easily, the shape of the containers should preferably have a wide opening and a narrow bottom, like that of centrifuge tubes. In some cases, such as when using mass spectrometry (MS) to determine the structure of proteins, the sample containers can be dialysis tubes, or may contain a dialysis membrane so that the small ions can be removed as inorganic ions are non-volatile and MS is quite sensitive to them.

The thermal insulator 30 can be foam or any other suitable materials. Its purpose is to separate the two thermostats 11 and 12 effectively so that the heat produced is mainly dissipated through the wires 20, and therefore facilitate the control of the growth of crystals.

Besides concentrating aqueous solutions, the present invention can be used to concentrate organic solutions and solids, such as benzene, xylene and phenol.

Those skilled in the art will recognize that the foregoing description provide a method and a device which can concentrate a plurality of samples simultaneously based on crystallization. In the examples which follow, the ability of the present device to concentrate minute amounts of analytes in aqueous solutions is demonstrated.

EXAMPLE 1

In this experiment the performance of the device of the present invention is demonstrated to concentrate five inorganic anions ($Cl^-$, $SO_4^{2-}$, $NO_3^-$, $NO_2^-$ and $Br^-$, each at the concentration of 0.1 µg/mL) in high purity water. A slush bath (prepared by mixing ethanol with dry ice) with a temperature of −70° C. was chosen as the thermostat 11, and a water bath (room temperature 25° C.) was used as the thermostat 12. The copper wires 20 were of diameter 1 mm. Eppendorf tubes with a volume of 500 µL were used as the sample containers 50. Time of concentration was recorded when the slush bath was poured into the thermostat 11.

Figure 3:
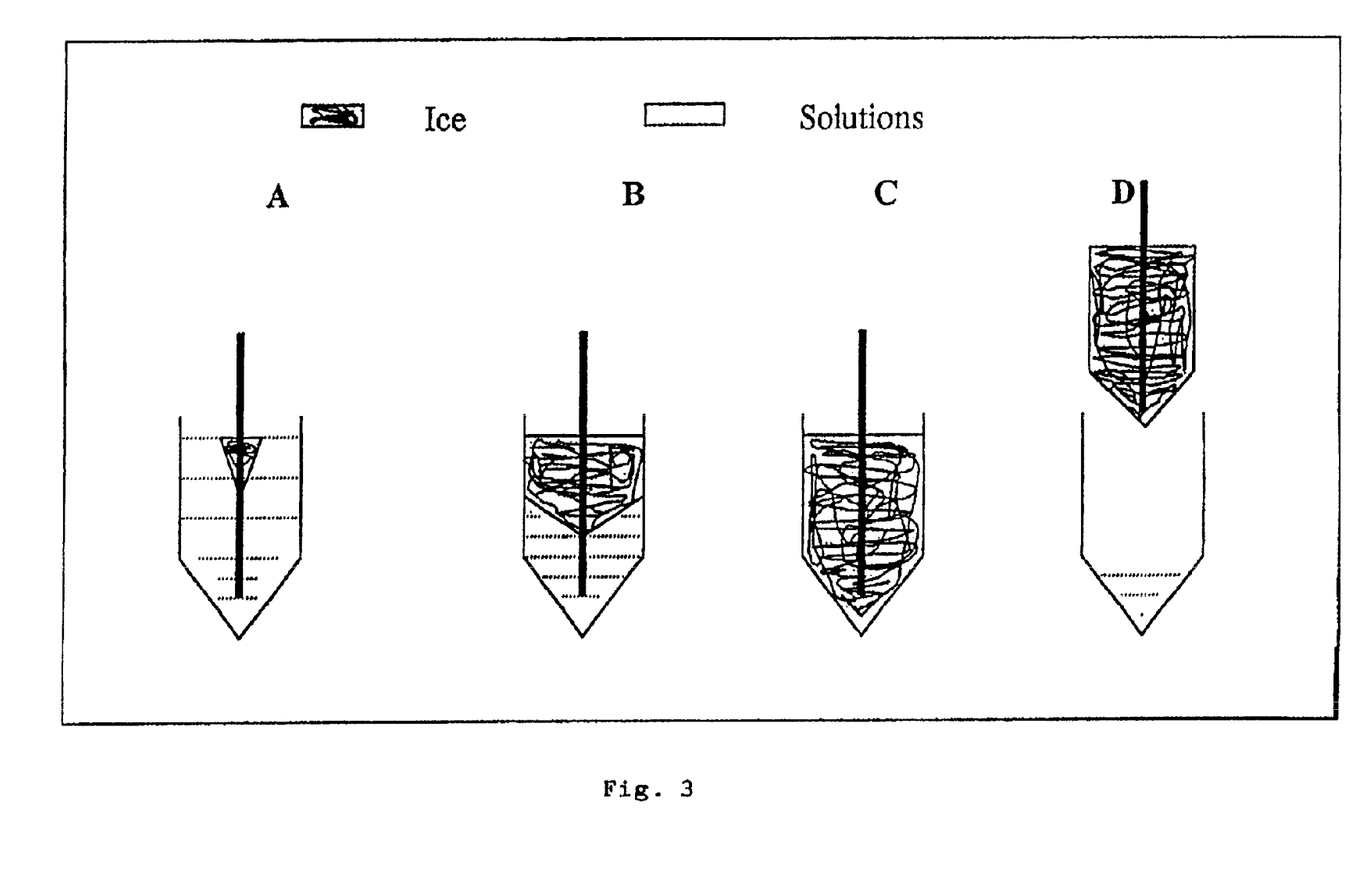
FIGS. 3A to 3D illustrates the process of ice growth and separation from the concentrated solutions during freeze concentration, taking one sample container as an example.
Figure 4:
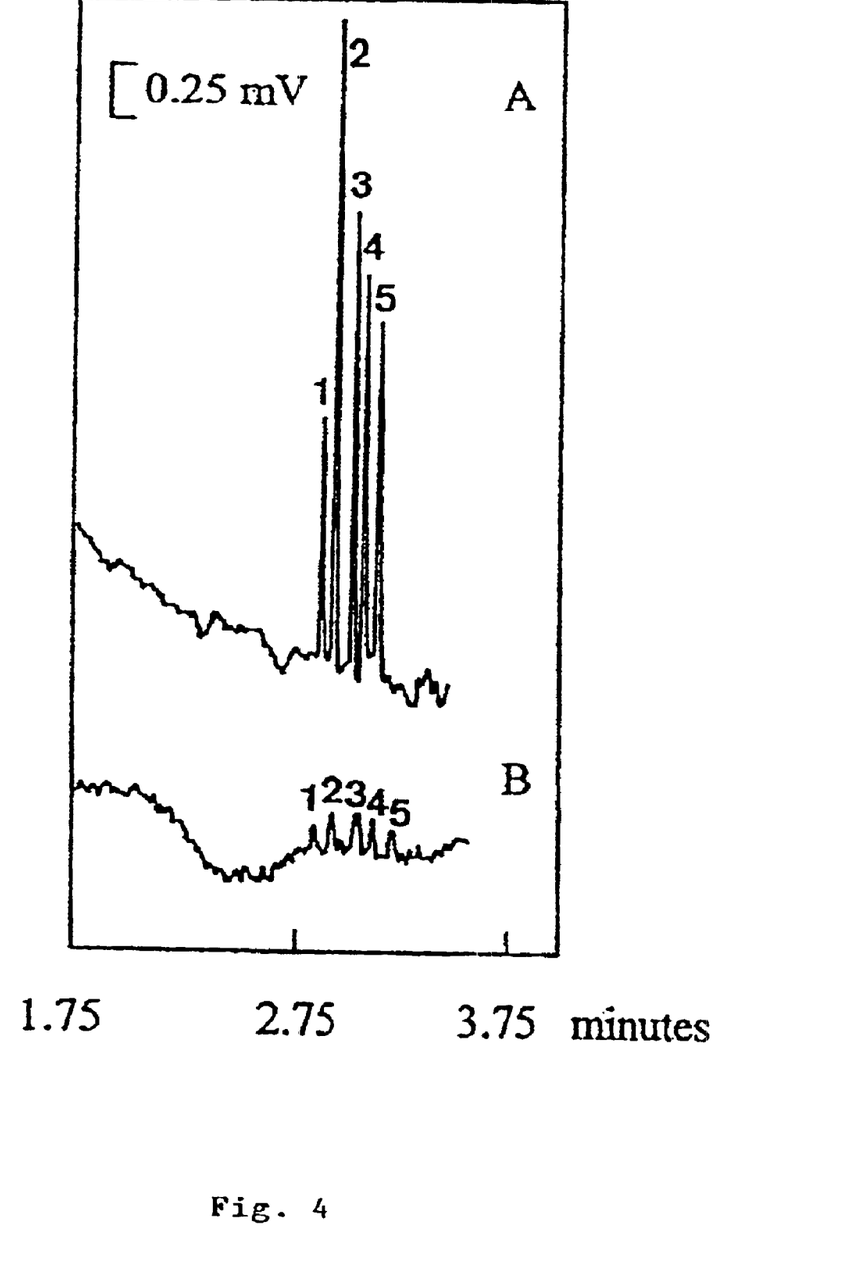
FIG. 4 is the typical electropherograms, obtained by capillary electrophoresis, of five kinds of inorganic anions before and after applying the freeze concentration process of the present invention.

FIG. 3 is a schematic diagram illustrating the changes of the sample solutions in the sample containers 50 during freeze concentration (FIGS. 3A, 3B, and 3C show the changes at 1, 5 and 7 minutes after the slush bath was added into the hemostat 11. FIG. 3D shows the final stage when the ice and the wires 20 were separated from the concentrated solutions remaining in the sample containers 50.). From FIG. 3, it can be seen that the ice came out first on the wires 50 and then spread into other areas of the solutions. With the anions continuously rejected from the ice front, they were concentrated in the remaining solutions. The whole process was finished in 8 minutes. FIG. 4A shows the electropherogram of the sample before concentration. FIG. 4B shows the electropherogram obtained after applying the freeze concentration process of the present invention. It can be seen that nearly 15 times concentration was obtained.

EXAMPLE 2

Figure 5:
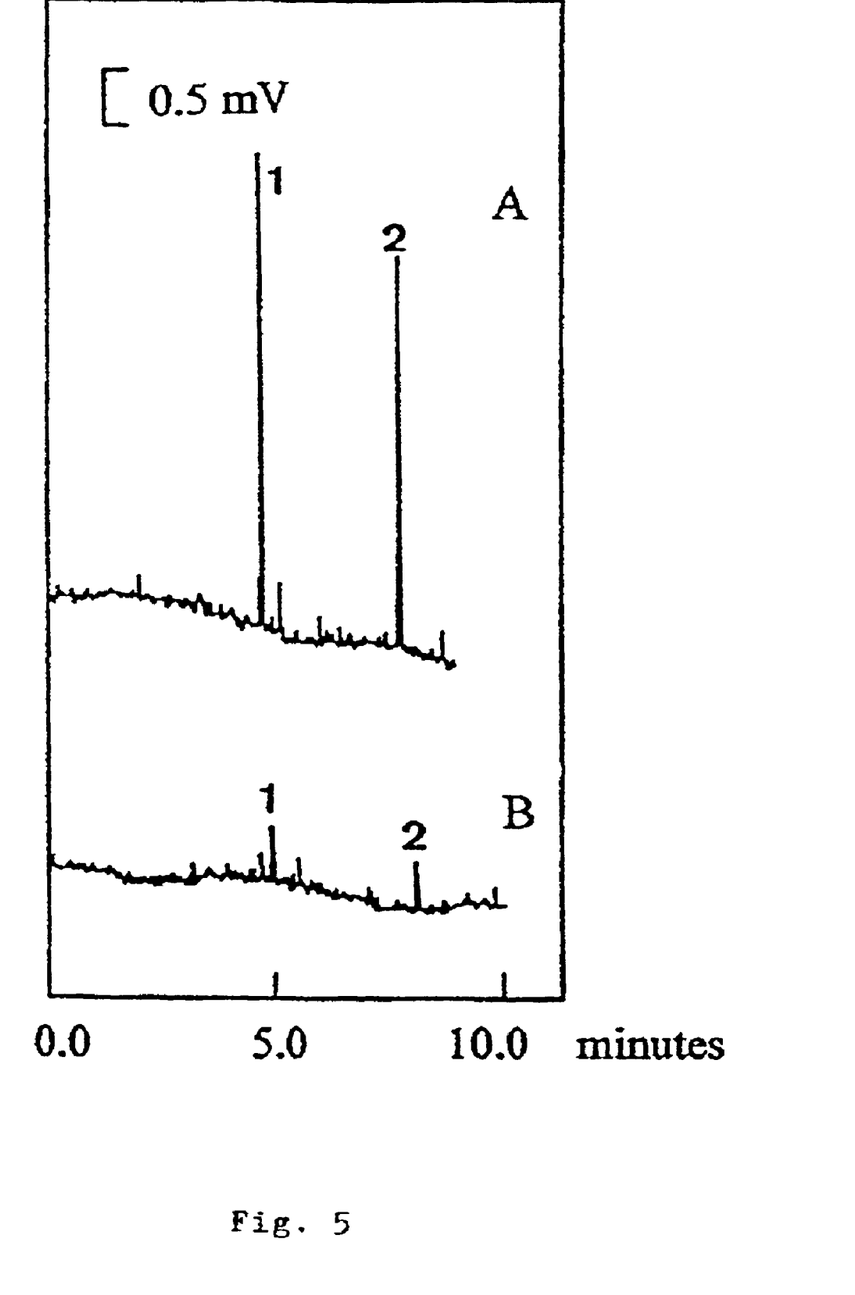
FIG. 5 is the typical electropherogranms, obtained by capillary electrophoresis, of two phenols before and after applying the freeze concentration process of the present invention.

One of the advantages of freeze concentration is that it can be used to concentrate volatile and semi-volatile substances in aqueous solutions. In this example, two phenols (phenol and 3-chloro-phenol, at the concentration of 5 $\mu$g/ml each) were concentrated by the device of the present invention. The conditions used were the same as those in the example 1. FIG. 5A shows the electropherogram of the samples before concentration. FIG. 5B shows the electropherogram obtained after applying the freeze concentration process of the present invention. It can be seen that nearly 8 times concentration was obtained.

EXAMPLE 3

Figure 6:
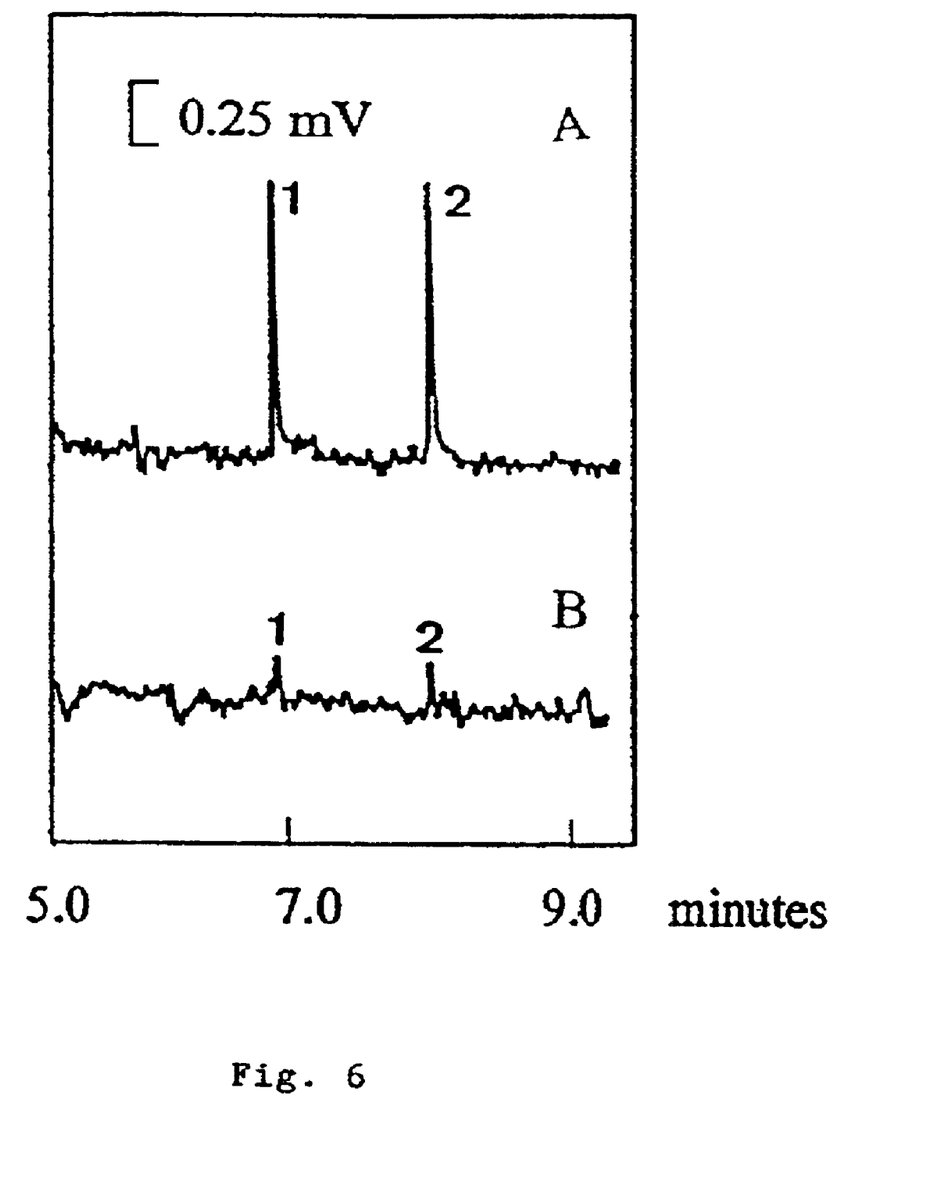
FIG. 6 is the typical electropherograms, obtained by capillary electrophoresis, of two proteins before and after applying the freeze concentration process of the present invention.

Many biological molecules, such as proteins and RNA, could be damaged during high temperature or organic solvents treatments. Freeze concentration can be a good choice for concentrating such thermally labile and chemically sensitive biological molecules because it doesn't involve any high temperature or organic solvents. This example demonstrates concentrating two proteins (Lysozyme and Trypsin, at the concentration of 12.5 $\mu$g/mL and 17.5 $\mu$g/mL, respectively) using the device of the present invention. First the concentration of the protein solution by the conditions in the examples 1 and 2 was tested. Small concentration efficiency (about 1.5 times) was obtained. The reason may be due to the low diffusion coefficient of the proteins. The growth rate of the ice in the above conditions was significantly faster and may be larger than the diffusion rate of the proteins. Therefore, much of the protein molecules were included into the ice lattice. As such, the growth rate of the ice during freeze concentration was lowered. After using a slush bath (prepared by mixing ethylene glycol with dry ice) with a temperature –15° C. as the thermostat 11, nearly 100% recovery for both proteins was obtained. FIG. 6A shows the electropherogram of the samples before concentration. FIG. 6B shows the electropherogram obtained after applying the freeze concentration process of the present invention. It can be seen that nearly 12 times concentration was obtained.

EXAMPLE 4

Figure 7:
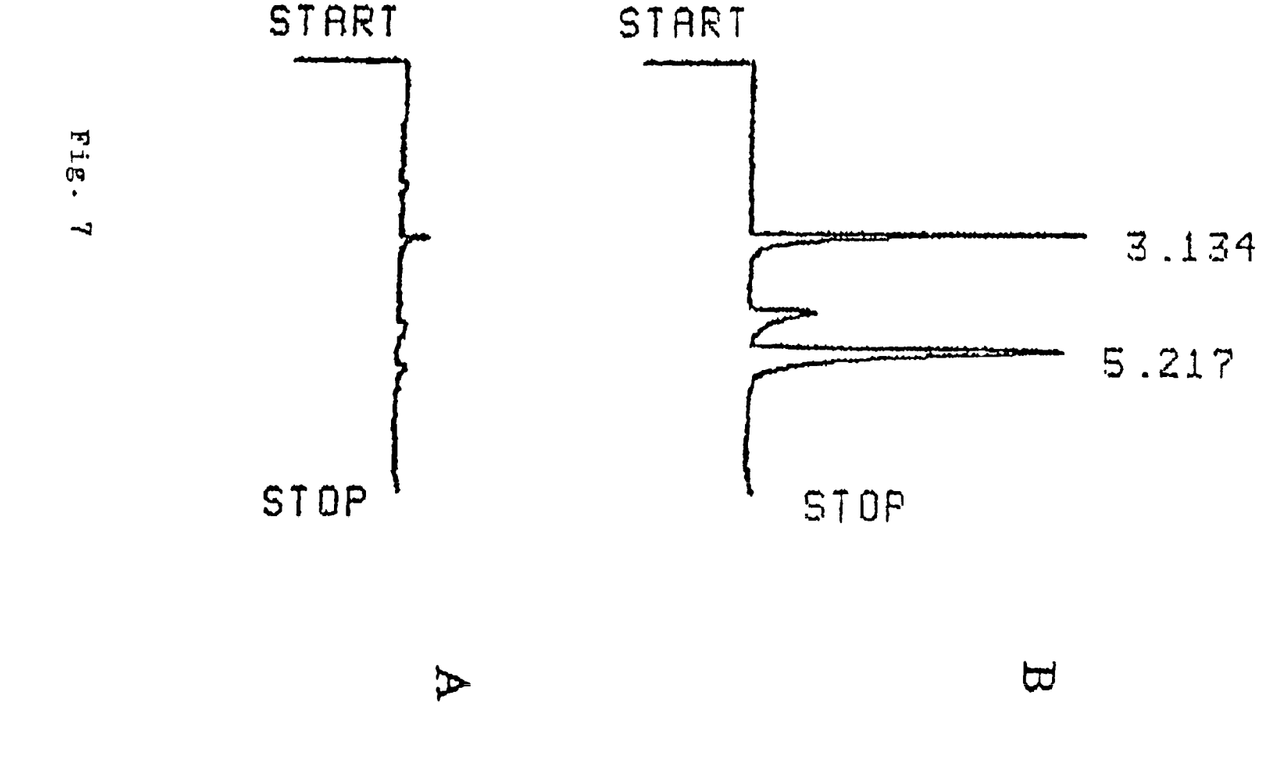
FIGS. 7A and 7B are the chromatographs, obtained by gas chromatography, of organic solvents in wastewater before and after applying the freeze concentration process of the present invention.

This example illustrates that the present invention may be used to analyze real samples which are considered to be difficult by the current concentration methods. Methanol, ethanol and acetone are widely used raw materials because they are good solvents for many chemicals. Their concentrations in industrial wastewater and surface water have been increasing with the development of chemical industries. It is important to know their concentrations in wastewater in order to control these contaminants. Usually their concentrations need to be below 1 ppm after treatment of the wastewater. Because they are quite hydrophilic, solid phase extraction does not work well in this case. Suitable solvents have also not been found to extract them. However, it is quite easy to concentrate them using the present invention. In a particular example, a wastewater taken from a chemical company was filtered first through a 0.4 $\mu$m nylon membrane to remove solids in the solution. After filtration, 0.5 ml solution was filled into the Eppendorf tube in order to apply freeze concentration. Other conditions for freeze concentration were the same as that in example 1. The concentrated solution after concentration was injected directly into a GC instrument (HP series 5890 plus) to measure the concentration of acetone, ethanol and methanol. FIG. 7B shows the results after concentration using the present invention. FIG. 7A is the chromatograph of the solution after filtration. It can be seen from FIG. 7 that the present invention can be used directly to preconcentrate trace amounts of methanol, ethanol and acetone in wastewater for their analysis.

The foregoing description of specific embodiments of this invention have been presented for purposes of illustration and description. They are not intended to be exhaustive or to limit the invention to the precise forms disclosed, and many modifications and variations are possible in light of the above teaching. It is intended that the scope of the invention be defined by the claims appended hereto and their equivalents.

REFERENCES

Patent Documents
1) SU 1228015 30 Apr. 1986 Dmitrichen M. M.
2) BE 794743/U.S. Pat. No. 3,897,409 29 Jul. 1975 Bayer A G Other Publications
1) Z. Zhou, E. Zheng, and D. Feng, "Determination of trace amount of organic solvent in water by freezing precencentration—gas chromatography", Nanjing Huagong Xueyuan Xuebao; Vol. 16, No. 1 (January 1994), pp. 67–71.
2) V. V. Aliseichik, A. B. Blank and L. V. Vasetskaya, "Determination of anion impurities in high-purity water by ion chromatography with crystallization preconcentration", Khim. Tekhnol. Vody, Vol. 14, No. 9 (September 1992), pp. 674–712.

What is claimed is:

1. A device for concentrating a plurality of samples comprising:
   a first temperature means having a plurality of containers for said plurality of samples;
   a second complimentary temperature means having a plurality of thermal conducting means comprising a plurality of wires which are adapted to be inserted in respective samples in said plurality of containers; and
   insulating means for insulating said first temperature means from said second temperature means such that an amount of heat from said plurality of samples is dissipated through said plurality of thermal conducting means,
   wherein said first and second temperature means are individually selected from circulating heaters and coolers, heating and cooling blocks or slush baths.

2. The device according to claim 1, wherein said plurality of containers are located in a face of said first temperature means and wherein said insulating means comprises a layer of insulating material disposed on a face of said second temperature means opposing said face of said first temperature means, said plurality of thermal conducting means passing from said second temperature means through said insulating material and, in use, into said plurality of samples in said plurality of containers.

3. The device according to claim 1, wherein said insulating means partly or completely prevents transfer of heat between said first temperature means and said second temperature means.

4. The device according to claim 1, wherein said insulating means comprises a plastic foam insulator.

5. The device according to claim 1, wherein said plurality of wires are formed from metal, polymer, inorganic or organic material.

6. The device according to claim 5, wherein said wires comprise copper wires or copper wires having an outer protective layer.

7. The device according to claim 1, wherein each of said wires has a diameter of from about several nanometers to several centimeters.

8. The device according to claim 7, wherein said each of said wires has a diameter of about 1 mm.

9. The device according to claim 1, wherein said plurality of containers comprises a plurality of wells each of which receives one of said plurality of samples or is adapted to receive a sample container holding one of said plurality of samples.

10. The device according to claim 9, wherein each sample container comprises a tube, bottle or vial.

11. The device according to claim 10, wherein each sample container comprises a dialysis tube.

12. The device according to claim 1, wherein said first and/or second temperature means are manually or automatically moveable from a loading position in which samples are loaded into said container means, to an operative position in which said conducting means are inserted into respective samples.

* * * * *